United States Patent
Mahó et al.

[11] Patent Number: 5,547,949
[45] Date of Patent: Aug. 20, 1996

[54] STEROIDS WITH PREGNANE SKELETON, PHARMACEUTICAL COMPOSITIONS CONTAINING THEM

[75] Inventors: Sándor Mahó; Zoltán Tuba; Anikó Gere; Pal Vittay; Béla Kiss; Éva Pálosi; László Szporny; Erzsébet C. Francsicsné; Anna M. Boórné; Gábor Balogh; Sándor Görög, all of Budapest, Hungary

[73] Assignee: Richter Gedeon Vegyeszeti Gyar Rt., Budapest, Hungary

[21] Appl. No.: 351,448

[22] PCT Filed: Jun. 8, 1993

[86] PCT No.: PCT/HU93/00035

§ 371 Date: Dec. 8, 1994

§ 102(e) Date: Dec. 8, 1994

[87] PCT Pub. No.: WO93/25570

PCT Pub. Date: Dec. 23, 1993

[30] Foreign Application Priority Data

Jun. 9, 1992 [HU] Hungary ................... 1910/92

[51] Int. Cl.[6] .............. C07J 43/00; A61K 31/56
[52] U.S. Cl. .............. 514/176; 540/106; 540/107
[58] Field of Search .............. 540/106, 107; 514/176

[56] References Cited

U.S. PATENT DOCUMENTS 5,099,019  3/1992  Mc Call et al. ................ 544/295

FOREIGN PATENT DOCUMENTS

| A10263213 | 4/1988 | European Pat. Off. |
| A10389368 | 9/1990 | European Pat. Off. |
| A10389370 | 9/1990 | European Pat. Off. |
| WOA191/11453 | 8/1991 | WIPO |

OTHER PUBLICATIONS

J. Med. Chem. 33(4), pp. 1145 to 1151 (1990).

*Primary Examiner*—Nicholas Rizzo
*Attorney, Agent, or Firm*—Herbert Dubno; Jonathan Myers

[57] ABSTRACT

Novel, therapeutically active 21-aminosteroids of formula (I)

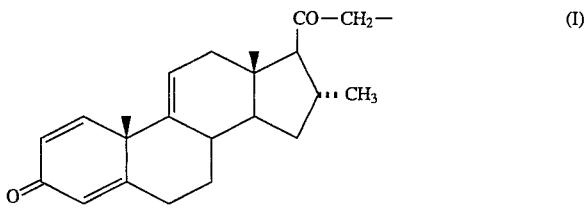

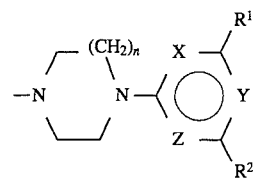

with pregnane skeleton, are disclosed wherein two of X, Y and Z are a nitrogen atom each and the third one is a methine group; $R^1$ and $R^2$ are independently from each other, a primary amino group bearing as substituent a branched-chain $C_{4-8}$alkyl -alkenyl or -alkynyl group, or a $C_{4-10}$cycloalkyl group comprising 1 to 3 ring(s) and being optionally substituted by at least one $C_{1-3}$alkyl group; or $R^1$ and $R^2$ are each a spiro-heterocyclic secondary amino group containing at most 10 carbon atoms and optionally at least one oxygen atom as additional heteroatom; or one of $R^1$ and $R^2$ is an unsubstituted heterocyclic secondary amino group containing 4 to 7 carbon atoms and the other one is an above-identified primary amino group, an above-identified spiro-heterocyclic secondary amino group, or a heterocyclic secondary amino group containing 4 to 7 carbon atoms and substituted by at least one $C_{1-4}$alkyl group; and n is 1 or 2, as well as their acid addition salts and pharmaceutical compositions containing these compounds.

4 Claims, No Drawings

STEROIDS WITH PREGNANE SKELETON, PHARMACEUTICAL COMPOSITIONS CONTAINING THEM

This application is a 371 of PCT/HU93100035 filed Jun. 8, 1993.

FIELD OF THE INVENTION

The invention relates to novel therapeutically active 21-aminosteroids of the formula

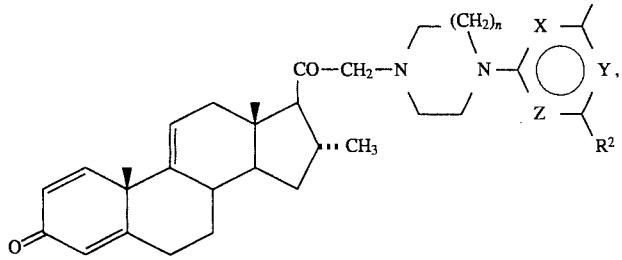

with pregnane skeleton, wherein two of X, Y and Z are each a nitrogen atom each and the third one is a methine group;

$R^1$ and $R^2$ are each, independently from each other, a primary amino group bearing as substituent a branched-chain $C_{4-8}$alkyl, -alkenyl or -alkynyl group, or a $C_{4-10}$cycloalkyl group comprising 1 to 3 ring(s) and being optionally substituted by $C_{1-3}$alkyl group(s); or $R^1$ and $R^2$ are each a spiro-heterocyclic secondary amino group containing at most 10 carbon atoms and optionally at least one oxygen atom as additional heteroatom; or one of $R^1$ and $R^2$ is an unsubstituted heterocyclic secondary amino group containing 4 to 7 carbon atoms and the other one is an above-identified primary amino group, an above-identified spiro-heterocyclic secondary amino group, or a heterocyclic secondary amino group containing 4 to 7 carbon atoms and substituted by $C_{1-4}$-alkyl group(s); and n is 1 or 2, as well as their acid addition salts and pharmaceutical compositions containing these compounds.

Furthermore, the invention relates to a process for the preparation of the above compounds.

The compounds of the formula (I) according to the invention are new and possess a valuable biological activity, an antioxidant (lipid peroxidation-inhibiting) effect, when investigated under in vitro conditions. Some representatives of them show a remarkable effectivity in vivo on the cerebral trauma model.

Accordingly, the invention relates also to a method of treatment which comprises administering a therapeutically effective amount of a compound of the formula (I) or a pharmaceutically acceptable acid addition salt thereof into the organism of a patient for inhibiting the peroxidation of lipids.

Hereinafter and in the claims primary amino groups are meant to contain a hydrogen atom as one substituent whereas the other substituent is a branched-chain $C_{4-8}$alkyl, -alkenyl or -alkynyl group, or a $C_{4-10}$cycloalkyl group, comprising 1 to 3 rings, and being optionally substituted by $C_{1-3}$-alkyl group(s). The branched-chain $C_{4-8}$alkyl, -alkenyl and -alkynyl groups may be various iso-, sec- and tert-butyl, butenyl, pentyl, pentenyl, pentynyl, hexyl, hexenyl, hexynyl, pentyl, heptenyl, heptynyl, octyl, octenyl and octynyl groups. Preferred representatives of these are the 1,1-dimethylethyl, 2,2-dimethylpropyl and 2,2-dimethyl-4-penten-1-yl groups.

The $C_{4-10}$cycloalkyl group comprising 1 to 3 rings and being optionally substituted by $C_{1-3}$alkyl group(s) can be e.g. a cyclobutyl, cyclopentyl, cyclohexyl, cycloheptyl or adamantyl group. These groups may be unsubstituted or bear one or more methyl, ethyl or propyl group(s) as substituents.

As $R^1$ and $R^2$, the spiro-heterocyclic secondary amino group containing at most 10 carbon atoms and optionally at least one additional oxygen heteroatom is exemplified by the 4,4-ethylenedioxy-1-piperidinyl group, without any limitation thereto.

When representing an unsubstituted heterocyclic secondary amino group containing 4 to 7 carbon atoms, one of $R^1$ and $R^2$ may preferably be a pyrrolidino, piperidino or azepino group. In this case, the other one of $R^1$ and $R^2$ means either a primary amino group mentioned above, or an above-defined secondary heterocyclic group having spiro structure, or an above-defined heterocyclic secondary amino group containing 4 to 7 carbon atoms and substituted by $C_{1-4}$ alkyl group(s). These $C_{1-4}$ alkyl groups may be the same or different, e.g. methyl, ethyl, n- or isopropyl, or n-, iso-, sec- or tert-butyl groups. A preferred representative of these substituted heterocyclic secondary amino groups is e.g. the 2,2,6,6-tetramethyl-1-piperidinyl group.

BACKGROUND OF THE INVENTION

There are a large number of pat hological processes known, in the case of which extremely reactive free radicals are accumulated. The formation of these free radicals leads to the oxidation of unsaturated fatty acids (lipid peroxidation), which are important components of the cell membranes. This is a less specific, cell-destroying process altering or damaging the biomolecules. In this process functions of various levels of cells, organs or the whole organism may suffer injuries.

Due to their lipid peroxidation-inhibiting effect, antioxidant compounds assure protection against injuries induced by free radicals.

Active agents of compositions belonging to this structural and pharmacological group are believed to be incorporated to the membrane of neurons or glian cells and thereto counter balance pathomechanisms connected with lipid peroxidation which is a consequence of formation of reactive free oxygen radicals. The formation of such radicals is considered to play a decisive role in pathologic processes induced by injuries, accompanied by cell death. Since the role of the mechanisms mentioned is widespread and can be considered to the general in nearly all sectors of molecular pathology or pathobiology, respectively, it is obvious that any potential therapeutic utility of lipid peroxidation-inhibiting compounds should be in connection with an especially extended and diversified spectrum of syndromes, pathological pictures and disease groups.

Thus, compounds inhibiting the lipid peroxidation may have a therapeutical benefit not only in acute injuries (such as brain concussion, brain contusion, cerebral maceration, brain compression) or in acute shock of the brain circulation (arterial or venous thromboses, brain embolism, subarachnoidal haemorhages) but also in a number of other pathologic alterations or conditions affecting the central nervous system or other organ systems. The potential area of indication may involve such neuropsychiatric pathologic pictures as the Alzheimer's disease and Alzheimer-type dementiae, alcoholic dementia and central nervous system injuries accompanying the alcoholism, some so-called "negative" symptoms of schizophrenia, Parkinson's disease and Parkinson syndrome, amyotrophic lateral sclerosis, sclerosis multiplex, cluster headache as well as complications accompanying the neoplastic alterations of the brain.

Potential indications of using lipid peroxidation-inhibiting compounds in pathologic pictures of non-central nervous system origin may be e.g. forms of various severity of irradiation damages, septic or endotoxic shock, haemorrhagic shock, traumatic shock, stress-ulcus occurring as a consequence of major laesions, burn shock, conditions following extended surgical interventions, conditions following cardiopulmonar reanimation, reperfusion following organ transplantation, prevention of retrolental fibroplasia connected with the oxygen therapy of immature newburns, protection from the adriamycin cardiotoxicity, prevention of the reperfusion injury occurring as a complication of acute myocardial infarction (e.g. after thrombolytic treatment), some allergic reactions, insect bites, inflammatory processes of the skin (e.g. psoriasis, eczema), nephrosis syndrome (of immunological origin), rheumatoid arthritis, systematic lupus erythematosus, endogenic uveitis, bronchial asthma, emphysema as well as atherosclerosis of the blood vessels.

The importance of such compounds inhibiting lipid peroxidation is proven also by the high number of the most recent literature references (patent applications as well as scientific publications).

In the published PCT patent application No. WO 87/01706 the preparation of mainly aminosteroids is described, wherein an "amino group" is bound to the terminal carbon atom of the C-17 side chain. Double bond(s) in position 4 or positions 1,4 of ring A of the steroid skeleton, oxo- or hydroxyl group in position 3, α- or β-alkyl group or halogen in position 6 and chiefly α-hydroxyl group in position 11 as well as α- or β-methyl group in position 16 and a double bond in position 9(11) are present. The ring of the steroid skeleton may be saturated or aromatic. Some 21-aminosteroids are also described in which the double bond is present in position 17(20). In the case of compounds disclosed in this publication the disubstituted pyrimidine, triazine or pyridine ring is bound in the most cases through a piperazinyl group to the position 21. Among the compounds published 16α-methyl- 21-{4-[2,4-bis(pyrrolidino)-6-pyrimidinyl]-1-piperazinyl}pregna-1,4,9(11)-triene 3,20-dione methanesulfonate (generic name: tirilazad mesylate) is in the second stage of clinical trials at present.

Similarly, the synthesis of steroid lipid peroxidation-inhibiting compounds is described in the published PCT application No. WO 87/07895. The synthesis of "amino esters" and "corticoid amino esters", above all "17-amino esters", "11,17-bis(amino) esters", "3,17-bis(amino) esters", "11-amino esters" and "3-amino esters", all of androstane structure, is discussed. According to this publication these compounds may be useful as inhibitors of lipid peroxidation occurring as consequences of spinal, cephalic and other injuries. The amino substituents have a structure similar to those mentioned in the preceding publication.

The preparation of novel "amino-9,10-secosteroids" is described in the published PCT patent application No. WO 88/07527. The amino substituent is bound to the terminal carbon atom of the C-17 side chain of the secosteroid. The amino substituents are similar to those described in the preceding publications.

The synthesis of lipid peroxidation-inhibiting compounds is described in the published European patent applications Nos. 0,389,368, 0,389,369 and 0,389,370, too.

The preparation of corticoid-type "21-aminosteroids" is described in the published European patent application No. 0,389,368. For example, a 4-[2,5-bis(diethylamino)-6-pyridinyl]-piperazinyl group may be bound to the C-21 carbon atom. The ring A of the sterane skeleton contains one or two double bond(s) whereas substituents characteristic of the corticoids may be present in positions 6, 9, 11, 16 and 17. A double bond may be present in position 9(11), too.

The synthesis of "amine derivatives" of 3-oxo-19-norsteroids is described in the published European patent application No. 0,389,370. As specific compounds 17β-hydroxy-11β-(4-dimethylaminophenyl) -17α-{3-[4-[2,6-bis(pyrrolidino)- 4-pyrimidinyl]-1-piperazinyl]-1-propynyl}estra-4,9 -diene- 3-one, 17β-hydroxy-11β-(4-dimethylaminophenyl)-17α-{3-[4-[5,6-bis(diethylamino)-2-pyridyl]-1-piperazinyl]-1-propynyl}estra-4,9-diene-3-one, 17β-hydroxy-11β-(4-di-methylaminophenyl)- 17α-{3-[4-[2,6-bis(diethylamino)-2-pyridyl]-1-piperazinyl]-1-propynyl}estra-4,9-diene-3-one, 17β-hydroxy- 11β-(4-dimethylaminophenyl)-17α-{3-[4-[2,6-bis(1-pyrrolidinyl)-4-pyrimidinyl]-1-piperazinyl]-1-propynyl}estra-4,9-diene-3-one and 17β-hydroxy-11β-(4-dimethylaminophenyl)-17α-{3-[4-[2,6-bis(pyrrolidino)-4-pyrimidinyl]-1-piperazinyl]-1-propynyl}estra-4,9-diene-3-one are exemplified.

The synthesis of aminosteroid derivatives with androstane skeleton, similarly showing a lipid peroxidation-inhibiting affect, are described in the published European patent application 0,389,369; these compounds similarly possess a lipid peroxidation-inhibiting effect. Examples of such compounds are e.g. 11β,17β-dihydroxy-17α-{3-[4-[2,6-bis (pyrrolidino)-4-pyrimidinyl]-1-piperazinyl]-1-propynyl}-androsta-4,6-diene-3-one, 11β, 17β-dihydroxy-6-methyl-17α-{3-[4-[2,6-bis(pyrrolidino)-4-pyrimidinyl]-1-piperazinyl]-1-propynyl}androsta-1,4,6-triene-3-one, 11β, 17β-dihydroxy-6-methyl- 17α-{3-[4-[5,6-bis(dimethylamino)-2-pyridyl]-1-piperazinyl]- 1-propynyl}androsta-1,4,6-triene-3-one and 11β, 17β-dihydroxy- 6-methyl-17α-{3-[4-[3,6-bis(diethylamino)-4-pyridyl]- 1-piperazinyl]-1-propynyl}androsta-1, 4,6-triene-3-one.

In the published European patent application No. 0,156,643 primarily the synthesis of water-soluble corticosteroid derivatives is described which are mainly characterized thereby that the hydroxyl group or an ester derivative thereof in position 11 is in the α-configuration or a double bond is present in position 9(11). Among the compounds described 17α-hydroxy-11α-(2,2-dimethylpropylcarbonyloxy)-pregna- 1,4-diene-3,20-dione-21-yl succinate sodium salt is considered to be the most effective lipid peroxidation-inhibiting agent.

In the published PCT patent application No. WO 91/11453 bis("amino")pyrimidinyl-piperazinyl derivatives containing an oxygen function in position 5 are disclosed, wherein a steroid molecule, 3,4-dihydro-6-hydroxy-2,5,7,8-tetramethyl-2H-1-benzopyran-2-ylmethyl group or a derivative thereof may be connected to the nitrogen in position 1 of the piperazine moiety. In this description 5-hydroxypyrimidine derivatives substituted by an alkyl group are also described.

Logically, the preparation of lipid peroxidation-inhibiting compounds was extended to the investigation of amine derivatives containing a non-steroid skeleton. Thus, e.g. in the published PCT patent application No. WO 88/08424 the preparation of novel aromatic and aliphatic bicyclic amine, cycloalkylamine, quinone-amine, amino ether and bicyclic amino ether derivatives are described which may be useful e.g. for healing cephalic and spinal injuries. From the derivatives described 2-{[4-2,6-bis(1-pyrrolidinyl)-4-pyrimidinyl]-1-piperazinyl]methyl}-3,4-dihydro-2,5,7,8-tetramethyl- 2H-1-benzopyran-6-ol dihydrochloride was investigated in detail.

OBJECT OF THE INVENTION

The object of the present invention is the preparation of compounds showing higher biological effectivity and/or less toxicity in comparison to those known in the art. Namely, the properties mentioned result in a more advantageous therapeutical applicability in comparison to the active agents known in the art.

SUMMARY OF THE INVENTION

Surprisingly, it has been found that the novel 21-aminosteroids of formula (I), having a pregnane skeleton, possess the desired excellent lipid peroxidation-inhibiting effect.

The novel 21-aminosteroids of the formula (I) having a pregnane skeleton are prepared by acylating 21-hydroxy-16α-methylpregna-1,4,9(11)-triene-3,20-dione with 4-bromobenzenesulfonyl chloride or 4-nitrobenzenesulfonyl chloride, respectively, then reacting the obtained 21-substituted pregnane derivative of the formula

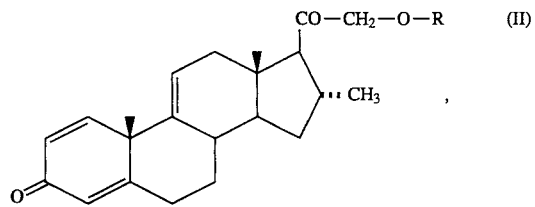

(II)

wherein R stands for 4-bromobenzenesulfonyl or 4-nitrobenzenesulfonyl group, with a piperazinyl-bis(alkylamino)pyrimidine derivative of the formula

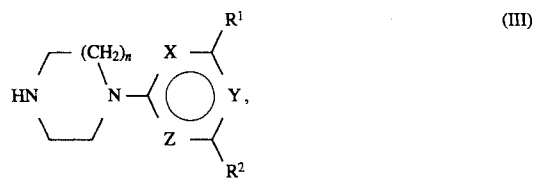

(III)

wherein X, Y, Z, $R^1$, $R^2$ and n are as defined above, and, if desired, liberating an obtained pregnane derivative of the formula (I), wherein X, Y, Z, $R^1$, $R^2$ and n are as defined above, from a salt and/or, if desired, transforming an obtained free base to an acid addition salt by reacting it with an appropriate acid.

21-(4-bromobenzenesulfonyloxy)-16α-methylpregna-1,4,9(11)-triene-3,20-dione and 16α-methyl-21-(4-nitrobenzenesulfonyloxy)-pregna- 1,4,9(11)-triene-3,20-dione of the formula (II) used as starting substances are also new compounds, which can be prepared as described hereinafter.

After dissolving 21-hydroxy-16α-methylpregna-1,4,9(11)-triene- 3,20-dione (known from the French patent specification No. 1,296,544) in tetrahydrofuran, triethylamine as well as an excess of 4-bromobenzenesulfonyl chloride or 4-nitrobenzenesulfonyl chloride, respectively, is added to the above solution at a temperature of about 0° C. The reaction is continued at room temperature for about additional 2 to 4 hours and after the reaction has become complete [which can be followed by thin layer chromatography (TLC)], the solution is portionwise added to water. After compacting the precipitate the mixture is filtered, the precipitate is washed with water up to neutral, then dried and recrystallized. The reaction of the obtained 21-substituted pregnane derivatives of the formula (II) with piperazinyl-bis(alkylamino)pyrimidine derivatives of the formula (III) is preferably carried out in such a way that 21-(4-bromobenzenesulfonyloxy)- 16α-methyl-pregna-1,4,9(11)-triene-3, 20-dione or 16α-methyl-21-(4-nitrobenzenesulfonyloxy)-pregna-1,4,9(11)-triene- 3,20-dione, respectively, is dissolved in a polar solvent, preferably acetone or acetonitrile, then the piperazinyl-bis (alkylamino)pyrimidine derivative of the formula (III) and potassium carbonate are added to the above solution. The reaction mixture is vigorously stirred at about 50° to 70° C. until the reaction becomes complete, then the solvent is distilled off, the evaporation residue is distributed between a halogenated hydrocarbon, preferably chloroform, and water. After separation the organic phase is washed several times with water, then dried. After evaporating the organic solvent from the anhydrous solution the residue is purified by chromatography on a silica gel column and subsequently, if desired, recrystallized.

The piperazinyl-bis(alkylamino)pyrimidine derivatives of the formula (III) are prepared in such a manner that 2,4,6-trichloropyrimidine is reacted with a primary or secondary amine corresponding to the $R^1$ or $R^2$ amino group in an ether-type solvent, e.g. tetrahydrofuran, in a temperature range from about −20° C. to about 40° C., for a time of about 30 minutes up to several days depending on the reactivity of the amine. In the case of the sterically hindered 2,2,6,6-tetramethylpiperidine (which can be used as solvent, too), a reaction lasting for about 50 hours at the boiling point of the reaction mixture is necessary for making the reaction complete. After termination of the reaction the solvent is distilled off, the residue is dissolved in a halogenated hydrocarbon, preferably chloroform, then washed with aqueous sodium hydroxide solution and water. After separation the organic phase is dried, the solvent is evaporated, the 4,6-dichloro-2-alkylaminopyrimidine as well as 2,6-dichloro-4-alkylaminopyrimidine derivatives formed in the reaction are separated by chromatography on a silica gel column. The separated isomers are purified by recrystallization. The thus obtained monoalkylamino-dichloropyrimidine isomers are again reacted with an amine being the same as or different from that used in the first step. The parameters of this reaction are primarily determined by the reactivity of the amine reactant. Thus, when reacting monoalkylamino-dichloropyrimidine derivatives with pyrrolidine, the reaction becomes complete at about room temperature whereas a reaction lasting for about 15 hours at about 130° C. is required for a reaction with tert-butylamine. The reaction of neopentylamine with monoalkylamino-dichloropyrimidines can be accomplished under milder reaction conditions: this reaction becomes complete by boiling in isopropanol for 20 hours. The less reactive 5-amino-4,4-dimethyl-1-pentene reacts with pyrimidine derivatives only at higher temperatures. The reaction of 1-aminoadamantane having a large space demand can be achieved by boiling in n-butanol for about 75 hours.

The bis(alkylamino)-chloropyrimidine derivatives formed in the second step can be recovered in the same way as described for the recovery of monoalkylamino-dichloropyrimidine derivatives.

The piperazinylpyrimidine derivatives of the formula (III) can be prepared by reacting bis(alkylamino)-chloropyrimidine derivatives with piperazine as follows. After dissolving the bis(alkylamino)-chloropyrimidine derivatives in a tertiary amine, preferably N-ethylmorpholine, the reaction mixture is boiled under reflux and nitrogen with an excess of piperazine for about 25 hours. After the reaction has become complete, N-ethylmorpholine used as solvent and the major part of the excess piperazine are distilled off, and water is added to the residue which is similarly distilled off. This distillation is continued under atmospheric pressure until the head temperature reaches 100° C. The residue is dissolved in chloroform and washed first with aqueous sodium hydroxide solution, then with water. After separation the organic phase is dried, the chloroform is evaporated and the residue is purified by chromatography on a silica gel column, then by recrystallization.

The pharmacological study of the pregnane derivatives of the formula (I) according to the present invention was carried out on unanesthetized mice by using a known experimental cephalic trauma model [J. Neurosurg. 62, page 882 (1980)] modified by us. In this study, the potential cerebroprotective effects of intravenous (i.v.) doses of the compounds were investigated.

A metal cleaver of defined weight was let fall onto a defined part of the scullcap surface of the experimental animals from a defined height under the force of gravity. Within 5 minutes following the closed cephalic injury induced by the cleaver, a suitable dose of the substance under test was injected to a tail vein of the animals and the neurological condition of the animals was evaluated in the 60th minute following the cephalic trauma. This evaluation was performed by using a simple grip test, by examination of the effect of trauma on the motor functions of both the upper and lower limbs. In addition, the frequency of cases considered to be "mild" or "severe", based on predetermined criteria, as well as the ratio of animals suffering from paraparesis-paraplegia were registered in the various treatment groups. The development of eventually occurring deficiency symptoms of the nervous system was made quantitative by comparison of the neurological condition of animals treated with the active agent to the condition of controls treated only with the vehicle.

When administered in the most favorable dose of 0.1 mg/kg, 21-{4-[2,4-bis(adamantylamino)-6-pyrimidinyl]-1-piperazinyl}- 16α-methylpregna-1,4,9(11)triene-3,20-dione methanesulfonate of formula (I) increased by 33% the number of cases signed as "mild" (based on the neurological symptoms induced by the cephalic trauma) and similarly, it decreased by 33% the frequency of cases involving paraparesis-paraplegia. The known tirilazad mesylate (see the published PCT patent specification No. WO 87/01706), chemically 16α-methyl-21-{4-[2,4-bis(pyrrolidino)-6-pyrimidinyl]-1-piperazinyl}pregna-1,4,9(11)triene-3,20-dione methanesulfonate, was used as control. When administered in the most effective dose of 0.3 mg/kg, tirilazad mesylate increased only by 23% the number of animals showing "mild" deficiency symptoms and decreased only by 20% the frequency of paraplegic animals.

Thus, it is obvious from the experimental results that the compounds according to our invention increase the lipid peroxidation-inhibiting effect exceeding those of known substances.

The novel 21-aminosteroid derivatives of the formula (I) having pregnane skeleton are used alone or in the form of their salts, suitably in the commonly used therapeutical compositions. These compositions may be in solid, liquid or semisolid state. Commonly used filling, diluting, stabilizing, pH- and osmotic pressure-influencing, flavoring and aromatizing as well as formulation-promoting or formulation-providing additives and auxiliaries can be used for the preparation of these compositions.

The solid pharmaceutical compositions may be e.g. tablets, dragées, capsules, cachets or powder ampoules useful for the preparation of injections. Liquid compositions are the injectable and infusable compositions, fluid medicines, packing fluids and drops. Semisolid compositions are ointments, balsams, creams, shaking mixtures and suppositories.

From the pharmaceutical composition an amount containing a dose of the active agent required to achieve the desired effect is administered to the patient. This dose depends on the stage of the disease, the severity of the pathological condition to be influenced, the weight of the patient, sensitivity of the patient against the active agent, route of administration and number of daily treatments. The dose of active agent to be used can safely be determined by the physician skilled in the art in the knowledge of the patient to be treated.

For the sake of a simple administration it is suitable if the pharmaceutical compositions comprise dosage units containing the amount of the active agent to be administered once, or a few multiples or a half, third or fourth part thereof. Such dosage units are e.g. tablets which can be provided with grooves promoting the halving or quartering of the tablet in order to exactly administer the required amount of the active agent.

Tablets can be coated with an acid-insoluble layer in order to assure the release of the active agent content after leaving the stomach. Such tablets are enteric-coated. A similar effect can be achieved also by encapsulating the active agent.

The pharmaceutical compositions containing the active agent according to the invention usually contain 1 to 100 mg of active agent in a single dosage unit. It is, of course, possible that the amount of the active agent in some compositions exceeds the upper or lower limits defined above.

The invention also relates to a method for inhibiting the peroxidation of lipids occurring in the organism. This method comprises administering a therapeutically effective amount of an active agent of the formula (I) or a pharmaceutically acceptable acid addition salt thereof to the patient.

The invention is illustrated in detail by the aid of the following non-limiting Examples.

EXAMPLE 1

Preparation of 21-(4-bromobenzenesulfonyloxy)-16α-methylpregna-1,4,9(11)-triene-3,20-dione After dissolving 10.0 g (29.4 mmoles) of 21-hydroxy-16α-methylpregna-1,4,9(11)-triene-3,20-dione in 100 ml of tetrahydrofuran, 7.14 ml (51.4 mmoles) of triethylamine, then at 0° C. 13.1 g (51.4 mmoles) of 4-bromobenzenesulfonyl chloride are added to the above solution and the reaction mixture is stirred at room temperature for 4 hours, then dropwise added to 450 ml of water while stirring. The precipitate is filtered off, dried and recrystallized from ether to give the title compound in a yield of 11.0 g (67.07%), m.p.:124°–129° C.

$^1$H-NMR (300 MHz, CDCl$_3$) δ ppm: 0.65 (s, 3H, 18-CH$_3$), 0.93 (d, 1H, 16α-CH$_3$), 1.40 (s, 3H, 19-CH$_3$), 4.54 and 4.66 (d, d, 2H, 21-CH$_2$), 5.5 (m, 1H, 11-H), 6.07 (t, 1H, 4-H), 6.29 (dd, 1H, 2-H), 7.16 (d, 1H, 1-H), 7.72 (d, 2H, phenylene C3-H, C5-H), 7.83 (d, 2H, phenylene C2-H, C6-H).

EXAMPLE 2

Preparation of
16α-methyl-21-(4-nitrobenzenesulfonyloxy)-pregna-1,4,9(11)-triene-3,20-dione After dissolving 10.0 g (29.4 mmoles) of 21-hydroxy-16α-methylpregna-1,4,9(11)-triene-3,20-dione in 100 ml of tetrahydrofuran, 7.14 ml (51.4 mmoles) of triethylamine, then at 0° C. 11.4 g (51.4 mmoles) of 4-nitrobenzenesulfonyl chloride are added to the above solution. Subsequently, the reaction mixture is stirred at room temperature for 2 hours, then dropwise added to 450 ml of water while stirring. The precipitate is filtered off, dried and recrystallized from ether to obtain the title compound in a yield of 13.5 g (87.66%), m.p.:151°–160° C.

$^1$H-NMR (300 MHz, CDCl$_3$) δ ppm: 0.67 (s, 3H, 18-CH$_3$), 0.94 (d, 1H, 16α-CH$_3$), 1.40 (s, 3H, 19-CH$_3$), 4.68 and 4.81 (d, d, 2H, 21-CH$_2$), 5.51 (m, 1H, 11-H), 6.07 (t, 1H, 4-H), 6.29 (dd, 1H, 2-H), 7.17 (d, 1H, 1-H), 8.17 (d, 2H, phenylene C2-H, C6-H), 8.42 (d, 2H, phenylene C3-H, C5-H).

EXAMPLE 3

Preparation of
4,6-dichloro-2-(1,1-dimethylethylamino)pyrimidine
and
2,6-dichloro-4-(1,1-dimethylethylamino)pyrimidine After dropwise adding 25 g (136.3 mmoles) of 2,4,6-trichloropyrimidine to a solution containing 31.52 ml (300 mmoles) of 1-amino-1,1-dimethylethane in 200 ml of tetrahydrofuran at a temperature between 10° and 15° C. while cooling under stirring, the reaction mixture is stirred at room temperature for an additional 5 hours and then evaporated. The residue is distributed between 500 ml of chloroform and 50 ml of 10% sodium hydroxide solution. After separation the organic phase is washed 4 times with 150 ml of water each, dried and evaporated. The residue is subjected to chromatography on a silica gel column and eluted with various mixtures of hexane and ethyl acetate. By using a 9:1 mixture as eluent 4,6-dichloro-2-(1,1-dimethylethylamino)pyrimidine is obtained which is recrystallized from hexane to give a yield of 11.35 g (37.84%), m.p.:70°–74° C.

$^1$H-NMR (60 MHz, THF-d$_8$) δ ppm: 6.63 (s, 1H, 5-H).

By further elution with a 4:1 mixture of hexane and ethyl acetate, the more polar 2,6-dichloro-4-(1,1-dimethylethylamino)pyrimidine is obtained which is recrystallized from ethyl acetate to give a yield of 13.31 g (44.35%), m.p.:192°–195° C.

$^1$H-NMR (60 MHz, THF-d$_8$) δ ppm: 6.32 (s, 1H, 5-H).

EXAMPLE 4

Preparation of
2,6-bis(1,1-dimethylethylamino)-4-chloropyrimidine

A solution of 5.0 g 4,6-dichloro-2-(1,1-dimethylethylamino)pyrimidine in 25 ml of 1-amino-1,1-dimethylethane is heated in a closed tube at 130° C. for 15 hours. Then, the reaction mixture is evaporated and the residue is distributed between 80 ml of chloroform and 15 ml of 10% sodium hydroxide solution. After separation the organic phase is washed 4 times with 20 ml of water each, then dried and evaporated. After recrystallization from hexane the title compound is obtained in a yield of 5.45 g (93.4%), m.p.:128°–130° C.

$^1$H-NMR (60 MHz, THF-d$_8$) δ ppm: 5.67 (s, 1H, 5-H).

EXAMPLE 5

Preparation of
2,4-bis(1,1-dimethylethylamino)-6-(1-piperazinyl) pyrimidine

A mixture containing 10.0 g (38.9 mmoles) of 4-chloro-2,6-bis(1,1-dimethylethylamino)pyrimidine, 13.42 g (155.8 mmoles) of piperazine and 150 ml of N-ethylmorpholine is boiled under reflux under nitrogen for 25 hours, then the solvent and piperazine are distilled off under atmospheric pressure. Water is added to the residue and distilled off until the head temperature reaches 100° C. After cooling down the residue is distributed between 200 ml of chloroform and 30 ml of 10% sodium hydroxide solution. After separation the organic phase is washed 4 times with 50 ml of water each, then dried and evaporated. The residue is purified by chromatography on a silica gel column by using a 9:1 mixture of chloroform and methanol. After recrystallizing the eluted product from hexane, the title compound is obtained in a yield of 7.65 g (64%), m.p.:142°–145° C.

$^1$H-NMR (60 MHz, CDCl$_3$) δ ppm: 4.99 (s, 1H, 5-H).

EXAMPLE 6

Preparation of
21-{4-[2,4-bis(1,1-dimethylethylamino)-6-pyrimidinyl]-1-piperazinyl}-16α-methylpregna-1,4,9(11)-triene-3,20-dione After adding 1.40 g (4.57 moles) of 2,4-bis(1,1-dimethylethylamino)-6-(1-piperazinyl}pyrimidine and 0.63 g of potassium carbonate to a solution containing 2.00 g (3.805 mmoles) of 21-(4-nitrobenzenesulfonyloxy)-16α-methylpregna-1,4,9(11)-triene-3,20-dione in 100 ml of acetone, the reaction mixture is boiled under reflux for 8.5 hours, then evaporated. The residue is distributed between 40 ml of chloroform and 10 ml of water. The chloroform layer is dried and evaporated. The residue is purified on a silica gel column by using a 98:2 mixture of chloroform/methanol as eluent. After recrystallization the title compound is obtained in a yield of 1.53 g (64%), m.p.:145°–155° C.

$^1$H-NMR (250 MHz, CDCl$_3$) δ ppm: 0.68 (s, 3H, 18-CH$_3$), 0.96 (d, 1H, 16α-CH$_3$), 1.39 (s, 18H, 2xNH-C(CH$_3$)$_3$), 1.40 (s, 3H, 19-CH$_3$), 3.13 and 3.23 (d, d, 2H, 21-CH$_2$), 4.99 (s, 1H, pyrimidine C5-H), 5.51 (m, 1H, 11-H), 6.07 (m, 1H, 4-H), 6.28 (dd, 1H, 2-H), 7.16 (d, 1H, 1-H).

EXAMPLE 7

Preparation of 4-chloro-2-(1,1-dimethylethylamino)-6-pyrrolidinopyrimidine

After adding in small portions 10 g of 4,6-dichloro-2-(1,1-dimethylethylamino)pyrimidine to 40 ml of pyrrolidine at a temperature below 10° C. under cooling while stirring, the reaction mixture is stirred at room temperature for 1 hour, then evaporated. After distributing the residue between 150 ml of chloroform and 30 ml of 10% sodium hydroxide solution, the organic phase is separated, washed 4 times with 50 ml of water each, then dried and evaporated. After recrystallization from ethyl acetate the title compound is obtained in a yield of 10.76 g (93%), m.p.:153°–157° C.

$^1$H-NMR (60 MHz, CDCl$_3$) δ ppm: 5.67 (s, 1H, 5-H).

EXAMPLE 8

Preparation of 2-(1,1-dimethylethylamino)-4-(1-piperazinyl)-6-pyrrolidinopyrimidine The reaction of 4-chloro-2-(1,1-dimethylethylamino)-6-pyrrolidinopyrimidine with piperazine, similarly as described in Example 5, gives the title compound in a yield of 78.1%, m.p.:162°–165° C.

$^1$H-NMR (60 MHz, CDCl$_3$) δ ppm: 4.87 (s, 1H, 5-H).

EXAMPLE 9

Preparation of 21-{4-[2-(1,1-dimethylethylamino)-6-pyrrolidino-4-pyrimidinyl]-1-piperazinyl}-16α-methylpregna-1,4,9(11)-triene 3,20-dione The reaction of 16α-methyl-21-(4-nitrobenzenesulfonyloxy)-pregna-1,4,9(11)-triene-3,20-dione with 2-(1,1-dimethylethylamino)-4-(1-piperazinyl)-6-pyrrolidinopyrimidine as described in Example 6 affords the title compound in a yield of 74.7%, m.p.:145°–170° C.

$^1$H-NMR (250 MHz, CDCl$_3$) δ ppm: 0.68 (s, 3H, 18-CH$_3$), 0.96 NC(CH$_3$)$_3$), 3.13 and 3.23 (d, d, 2H, 21-CH$_2$), 4.86 (s, 1H, pyrimidine C5-H), 5.51 (m, 1H, 11-H), 6.07 (br, 1H, 4-H), 6.28 (dd, 1H, 2-H), 7.16 (d, 1H, 1-H).

EXAMPLE 10

Preparation of 2-(1-adamantylamino)-4,6-dichloropyrimidine and 4-(1-adamantylamino)-2,6-dichloropyrimidine After adding 40.6 g (225.6mmoles) of 2,4,6-trichloropyrimidine to a solution of 70.3 g (465.6 mmoles) of 1-aminoadamantane in 650 ml of tetrahydrofuran, the reaction mixture is stirred for 24 hours, then the crystalline 1-aminoadamantane hydrochloride precipitate is filtered off, the filtrate is evaporated and the residue is subjected to chromatography on a silica gel column. By elution with a 9:1 mixture of hexane and acetone 2-(1-adamantylamino)-4,6-dichloropyrimidine is obtained,which is recrystallized from hexane to give a yield of 28.74 g (43.5%), m.p.:151°–155° C.

$^1$H-NMR (60 MHz, CDCl$_3$) δ ppm: 6.55 (s, 1H, 5-H).

By continuing the elution with a 24:1 mixture of hexane and acetone the more polar 4-(1-adamantylamino)-2,6-dichloropyrimidine is obtained which is recrystallized from hexane to result a yield of 35.56 g (53.8%), m.p.:193°–196° C.

$^1$H-NMR (60 MHz, CDCl$_3$) δ ppm: 6.33 (s, 1H, 5-H).

EXAMPLE 11

Preparation of 2,4-bis(1-adamantylamino)-6-chloropyrimidine

A solution of 26.0 g (87.25 mmoles) of 4,6-dichloro-2-(1-adamantylamino)pyrimidine and 39.5 g (261.6 mmoles) of 1-aminoadamantane in 200 ml of n-butanol, the reaction mixture is boiled under reflux for 24 hours, and evaporated. The residue is suspended in 400 ml of ether and filtered off. After drying, the filtered-off residue is purified by chromatography on a silica gel column and eluted with chloroform. After recrystallization from ether, the title compound is obtained in a yield of 23.94 g (66.44%), m.p.: 232°–236° C.

$^1$H-NMR (60 MHz, CDCl$_3$) δ ppm: 5.64 (s, 1H, 5-H).

EXAMPLE 12

Preparation of 2,4-bis(1-adamantylamino)-6-(1-piperazinyl)pyrimidine 2,4-bis-(1-Adamantylamino)-6-chloropyrimidine is reacted with piperazine similarly as described in Example 5 to give the title compound in a yield of 83.36%, m.p.:168°–175° C.

$^1$H-NMR (60 MHz, CDCl$_3$) δ ppm: 4.97 (s, 1H, 5-H).

EXAMPLE 13

Preparation of 21-{4-[2,4-bis(1-adamantylamino)-6-pyrimidinyl]-1-piperazinyl}-16α-methylpregna-1,4,9(11)-triene-3,20-dione After adding 1.88 g (4.07 mmoles) of 2,4-bis(1-adamantylamino)-6-(1-piperazinyl)pyrimidine and 0.56 g of potassium carbonate to a solution containing 2.00 g (3.57 mmoles) of 21-(4-bromobenzenesulfonyloxy)-16α-methylpregna-1,4,9(11)-triene-3,20-dione in 100 ml of acetonitrile, the reaction mixture is stirred at a temperature of 65° C. for 5 hours, then evaporated. The residue is distributed between 40 ml of chloroform and 10 ml of water. After separation the chloroform layer is dried and evaporated. The residue is purified by chromatography on a silica gel column by using a 98:2 mixture of chloroform/methanol as eluent. After recrystallization from ether the title compound is obtained in a yield of 2.48 g (88.5%), m.p.:210°–220° C.

$^1$H-NMR (250 MHz, CDCl$_3$) δ ppm: 0.68 (s, 3H, 18-CH$_3$), 0.96 (d, 1H, 16α-CH$_3$), 1.40 (s, 3H, 19-CH$_3$), 3.13 and 3.23 (d, d, 2H, 21-CH$_2$), 4.98 (s, 1H, pyrimidine C5-H), 5.51 (m, 1H, 11-H), 6.07 (m, 1H, 4-H), 6.28 (dd, 1H, 2-H), 7.16 (d, 1H, 1,-H).

EXAMPLE 14

Preparation of 2-(1-adamantylamino)-4-chloro-6-pyrrolidinopyrimidine 2-(1-Adamantylamino)-4,6-dichloropyrimidine is reacted with pyrrolidine similarly as described in Example 7 to give the title compound in a yield of 86%, m.p.:178°–180° C.

¹H-NMR (60 MHz, CDCl₃) δ ppm: 5.62 (s, 1H, 5-H).

EXAMPLE 15

Preparation of
2-(1-adamantylamino)-4-(1-piperazinyl)-
6-pyrrolidinopyrimidine 2-(1-Adamantylamino)-4-chloro-6-pyrrolidinopyrimidine is reacted with piperazine as described in Example 5 to obtain the title compound in a yield of 69.7%, m.p.:160°–164° C.

¹H-NMR (60 MHz, CDCl₃) δ ppm: 4.87 (s, 1H, 5-H).

EXAMPLE 16

Preparation of
21-{4-[2-(1-adamantylamino)-6-pyrrolidino-
4-pyrimidinyl]-
1-piperazinyl}-16α-methylpregna-1,4,9(11)-triene-
3,20-dione The reaction of 21-(4-bromobenzenesulfonyloxy)-16α-methylpregna- 1,4,9(11)-triene-3,20-dione with 2-(1-adamantylamino)- 4-(1-piperazinyl)-6-pyrrolidinopyrimidine as described in Example 6 gives the title compound in a yield of 79.94%, m.p.:155°–172° C.

¹H-NMR (60 MHz, CDCl₃) δ ppm: 0.69 (s, 3H, 18-CH₃), 0.94 (d, 3H, 16α-CH₃), 1.41 (s, 3H, 19-CH₃), 4.89 (s, 1H, pyrimidine C5-H), 5.51 (m, 1H, 11-H), 6.08 (br, 1H, 4-H), 6.28 (dd, 1H, 2-H), 7.21 (d, 1H, 1-H).

EXAMPLE 17

Preparation of
4,6-dichloro-2-(2,2-dimethylethylamino)pyrimidine
and
2,6-dichloro-4-(2,2-dimethylethylamino)pyrimidine After dropwise adding 25 g (136.3 mmoles) of 2,4,6-trichloropyrimidine to a solution of 23.84 g (273.5 mmoles) of 1-amino-2,2-dimethylpropane in 200 ml of tetrahydrofuran at a temperature between 10° and 15° C. while cooling under stirring, the reaction mixture is stirred at room temperature for 30 minutes, then evaporated. The residue is distributed between 300 ml of chloroform and 50 ml of 10% sodium hydroxide solution. After separation the organic phase is washed 4 times with 100 ml of water each, dried and evaporated. The residue is subjected to chromatography on a silica gel column by using mixtures of hexane/ethyl acetate elution. By eluting with a 19:1 mixture, 4,6-dichloro-2-(2,2-dimethylpropylamino) pyrimidine is obtained which is recrystallized from a mixture of ether and hexane to give a yield of 13.60 g (42.6%), m.p.:63°–66° C.

¹H-NMR (60 MHz, CDCl₃) δ ppm: 6.60 (s, 1H, 5-H).

By further elution with a 6:1 mixture, the more polar 2,6-dichloro-4-(2,2-dimethylpropylamino)pyrimidine is obtained which is recrystallized from a mixture of ether and hexane to result in a yield of 14.24 g (44.6%), m.p.:77°–79° C.

¹H-NMR (60 MHz, CDCl₃) δ ppm: 6.33 (s, 1H, 5-H).

EXAMPLE 18

Preparation of
4-chloro-2,6-bis(2,2-dimethylpropylamino)pyrimidine

After adding 5 ml of 1-amino-2,2-dimethylpropane to a solution of 5.0 g of 4,6-dichloro-2-(2,2-dimethylpropylamino)pyrimidine in 25 ml of isopropanol the reaction mixture is boiled under reflux for 20 hours, then evaporated. The residue is distributed between 80 ml of chloroform and 15 ml of 10% sodium hydroxide solution. After separation the organic phase is washed 4 times with 20 ml of water each, then dried and evaporated. After recrystallization from hexane the title compound is obtained in a yield of 2.994 g (49.4%), m.p.:95°–98° C.

¹H-NMR (60 MHz, CDCl₃) δ ppm: 5.71 (s, 1H, 5-H).

EXAMPLE 19

Preparation of
2,4-bis(2,2-dimethylpropylamino)-6-(1-piperazinyl)
pyrimidine

The reaction of 4-chloro-2,6-bis(2,2-dimethylpropylamino)pyrimidine with piperazine as described in Example 5 gives the title compound in a yield of 51.1%, m.p.:138°–140° C.

¹H-NMR (60 MHz, CDCl₃) δ ppm: 4.98 (s, 1H, 5-H).

EXAMPLE 20

Preparation of
21-{4-[2,4-bis(2,2-dimethylpropylamino)-
6-pyrimidinyl]-1-piperazinyl}-16α-methylpregna-
1,4,9(11)-triene-3,20-dione 16α-Methyl-21-(4-nitrobenzenesulfonyloxy)-pregna-1,4,9(11)-triene-3,20-dione is reacted with 2,4-bis(1,1-dimethylethylamino)- 6-(1-piperazinyl)pyrimidine as described in Example 6 to obtain the title compound in a yield of 8.95%, m.p.:140°–150° C.

¹H-NMR (60 MHz, CDCl₃) δ ppm: 0.68 (s, 3H, 18-CH₃), 1.40 (s, 3H, 19-CH₃), 4.96 (s, 1H, pyrimidine C5-H), 5.51 (m, 1H, 11-H), 6.10 (br, 1H, 4-H), 6.28 (dd, 1H, 2-H), 7.20 (d, 1H, 1-H).

EXAMPLE 21

Preparation of
4-chloro-2-(2,2-dimethylpropylamino)-
6-pyrrolidinopyrimidine 4,6-Dichloro-2-(2,2-dimethylpropylamino)pyrimidine is reacted with pyrrolidine as described in Example 7 to give the title compound in a yield of 96.7%, m.p.:147°–150° C.

¹H-NMR (60 MHz, CDCl₃) δ ppm: 5.67 (s, 1H, 5-H).

EXAMPLE 22

Preparation of
2-(2,2-dimethylpropylamino)-4-(1-piperazinyl)-
6-pyrrolidinopyrimidine (2,2-Dimethylpropylamino)-4-chloro-6-pyrrolidinopyrimidine is reacted with piperazine as described in Example 5 to obtain the title compound in a yield of 76%, m.p.:118°–120° C.

¹H-NMR (60 MHz, CDCl₃) δ ppm: 4.83 (s, 1H, 5-H).

EXAMPLE 23

Preparation of 21-{4-[2-(2,2-dimethylpropylamino)-6-pyrrolodino-4-pirimidinyl]-1-piperazinyl}-16α-methylpregna-1,4,9(11)-triene-3,20-dione 16α-Methyl-21-(4-bromobenzenesulfonyloxy)-pregna-1,4,9(11)-triene-3,20-dione is reacted with 2-(2,2-dimethylpropylamino)-4-(1-piperazinyl)-6-pyrrolidinopyrimidine as described in Example 13 to obtain the title compound in a yield of 74.1%, m.p.:130° C.

$^1$H-NMR (60 MHz, CDCl$_3$) δ ppm: 0.68 (s, 3H, 18-CH$_3$), 0.93 (s, 9H, —C(CH$_3$)$_3$), 0.96 (s, 3H, 16α-CH$_3$), 1.39 (s, 3H, 19-CH$_3$), 4.85 (s, 1H, pyrimidine C5-H), 5.51 (m, 1H, 11-H), 6.06 (br, 1H, 4-H), 6.26 (dd, 1H, 2-H), 7.17 (d, 1H, 1-H).

EXAMPLE 24

Preparation of 4,6-dichloro-2-[(2,2-dimethyl-4-penten-1-yl)-amino]pyrimidine and 2,6-dichloro-4-[(2,2-dimethyl-4-penten-1-yl)amino]pyrimidine After adding 4.59 g (25 mmoles) of 2,4,6-trichloropyrimidine to the solution of 6.23 g (55 mmoles) of 5-amino-4,4-dimethyl-1-pentene in 50 ml of tetrahydrofuran at room temperature, the mixture is further stirred at the same temperature for 4 hours, then evaporated. After distributing the residue between 60 ml of chloroform and 5 ml of 10% sodium hydroxide solution the organic phase is separated, washed 4 times with 10 ml of water each, then dried and evaporated. The residue is separated by chromatography on a silica gel column by using mixtures of hexane and ethyl acetate for elution. By eluting with a 19:1 mixture of hexane/ethyl acetate oily 4,6-dichloro-2-[(2,2-dimethyl-4-penten-1-yl)amino]pyrimidine is obtained in a yield of 2.62 g (40.3%).

$^1$H-NMR (60 MHz, CDCl$_3$) δ ppm: 6.61 (s, 1H, 5-H).

By carrying out the elution with a 9:1 mixture of hexane/ethyl acetate the more polar 2,6-dichloro-4-[(2,2-dimethyl-4-penten-1-yl)amino]pyrimidine is obtained in oily form in a yield of 2.99 g (45.9%)

$^1$H-NMR (60 MHz, CDCl$_3$) δ ppm: 6.34 (s, 1H, 5-H).

EXAMPLE 25

Preparation of 4-chloro-2,6-bis](2,2-dimethyl-4penten-1-yl)amino]-6-yl)amino]pyrimidine After dissolving 2.5 g (9.61 mmoles) of 4,6-dichloro-2-[(4,4-dimethyl-4-penten-5-yl)amino]pyrimidine in 25 ml of n-butanol 2.29 g (10.2 mmoles ) of 5-amino-4,4-dimethyl-1-penten are added to the above solution, the reaction mixture is boiled under reflux for 10 hours, then evaporated. The residue is distributed between 50 ml of chloroform and 5 ml of 10% sodium hydroxide solution. After separation the organic phase is washed 4 times with 10 ml of water each, then dried and evaporated. The residue is purified by chromatography on a silica gel column by using a 19:1 mixture of hexane/ethyl acetate as eluent to give the oily title compound in a yield of 2.25 g (69.5%).

$^1$H-NMR (60 MHz, CDCl$_3$) δ ppm: 5.70 (s, 1H, 5-H).

Example 26

Preparation of 2,4-bis[(2,2-dimethyl-4-penten-1-yl)amino]-6-(1-piperazinyl)pyrimidine The reaction of 4-chloro-2,6-bis[(2,2-dimethyl-4-penten-5-yl)amino]pyrimidine with piperazine as described in Example 5 results in a yield of 73.2% of the title compound, m. p.: 72°–84° C.

$^1$H-NMR (60 MHz, CDCl$_3$) δ ppm: 4.83 (s, 1H, 5-H).

Example 27

Preparation of 21-{4-[2,4-bis(4,4-dimethyl-1-penten-5-yl)amino]-6-pyrimidinyl]-1-piperazinyl}-16α-methylpregna-1,4,9(11)-triene-3,20-dione 16α-Methyl-21-(4-bromobenzenesulfonyloxy)pregna-1,4,9(11)-triene-3,20-dione is reacted with 2,4-bis[(4,4-dimethyl-1-penten-5-yl)amino]-6-(1-piperazinyl)pyrimidine as described in Example 13 to obtain the title compound in a yield of 46%, m.p.:98°–100° C.

$^1$H-NMR (300 MHz, CDCl$_3$) δ ppm: 0.69 (s, 3H, 18-CH$_3$), 0.96 (d, 1H, 16α-CH$_3$), 1.40 (s, 3H, 19-CH$_3$), 3.12 and 3.21 (d, d, 2H, 21-CH$_2$), 4.92 (s, 1H, pyrimidine -5H), 5.51 (m, 1H, 11-H), 6.07 (m, 1H, 4-H), 6.28 (dd, 1H, 2-H), 7.17 (d, 1H, 1-H).

EXAMPLE 28

Preparation of 2-(4,4-ethylenedioxy-1-piperidinyl)-4,6-dichloropyrimidine and 4-(4,4-ethylenedioxy-1-piperidinyl)-2,6-dichloropyrimidine After dropwise adding 43.32 g (286 soles) of 1,4-dioxa-8-azaspiro[4,5]decane to a solution of 25 g (136.3 mmoles) of 2,4,6-trichloropyrimidine in 200 ml of tetrahydrofuran at 0° C., the reaction mixture is stirred at room temperature for 1 hour, then evaporated. The residue is distributed between 300 ml of chloroform and 100 ml of 10% sodium hydroxide solution. After separation the organic phase is washed 4 times with 100 ml of water each and evaporated. The residue is subjected to chromatography on a silica gel column by using chloroform as eluent. In the first stage the less polar 2-(4,4-ethylenedioxy-1-piperidinyl)- 4,6-dichloropyrimidine is eluted which is recrystallized from ethyl acetate to obtain a yield of 13.98 g (35.36%), m.p.:104°–105° C.

$^1$H-NMR (60 MHz, CDCl$_3$) δ ppm: 6.50 (s, 1H, 5-H).

By further elution the more polar 4-(4,4-ethylenedioxy-1-piperidinyl)-2,6-dichloropyrimidine is obtained which is recrystallized from ethyl acetate to give a yield of 20.98 g (53.04%), m.p.:133°–136° C.

$^1$H-NMR (60 MHz, CDCl$_3$) δ ppm: 6.40 (s, 1H, 5-H).

EXAMPLE 29

Preparation of 2,6-bis(4,4-ethylenedioxy-1-piperidinyl)-4-chloropyrimidine

After dissolving 2.0 g (6.89 mmoles) of 2-(4,4-ethylenedioxy- 1-piperidinyl)-4,6-dichloropyrimidine in 40 ml of n-butanol and adding 2.6 ml (17.23 mmoles) of 1,4-dioxa-8-azaspiro[4,5]decane, the reaction mixture is boiled under reflux for 4 hours, then evaporated. The residue is distributed between 50 ml of chloroform and 5 ml of 10% sodium hydroxide solution. After separation the organic phase is washed 4 times with 10 ml of water each, dried and evaporated. After recrystallization from hexane the title compound is obtained in a yield of 2.51 g (91.8%)d, m.p.:130°–131° C.

$^1$H-NMR (60 MHz, CDCl$_3$) δ ppm: 5.88 (s, 1H, 5-H).

EXAMPLE 30

Preparation of 2,4-bis(4,4-ethylenedioxy-1-piperidinyl)-6-(1-piperazinyl)pyrimidine 2,6-bis(4,4-Ethylenedioxy-1-piperidinyl)-4-chloropyrimidine is reacted with piperazine in the way described in Example 5 to obtain the title compound in a yield of 55.7%, m.p.:130°–140° C.

$^1$H-NMR (60 MHz, CDCl$_3$) δ ppm: 5.01 (s, 1H, 5-H).

EXAMPLE 31

Preparation of 21-{4-[2,4-bis(4,4-ethylenedioxy-1-piperidinyl)-6-pyrimidinyl]-1-piperazinyl}-16α-methylpregna-1,4,9(11)-triene-3,20-dione The reaction of 16α-methyl-21-(4-nitrobenzenesulfonyloxy)pregna-1,4,9(11)-triene-3,20-dione with 2,4-bis(4,4-ethylenedioxy-1-piperidinyl)-6-(1-piperazinyl)pyrimidine as described in Example 5 leads to the title compound in a yield of 77.5%, m.p.:156°–174° C.

$^1$H-NMR (60 MHz, CDCl$_3$) δ ppm: 0.67 (s, 3H, 18-CH$_3$), 0.94 (s, 3H, 16 α-CH$_3$), 1.38 (s, 3H, 19-CH$_3$), 3.99 (s, 8H, 2 x ethylenedioxy), 5.12 (s, 1H, pyrimidine C5-H), 5.5 (m, 1H, 11-H), 6.06 (br, 1H, 4-H), 6.25 (dd, 1H, 2-H), 7.15 (d, 1H, 1-H).

Example 32

Preparation of 4,6-dichloro-2-(2,2,6,6-tetramethyl-1-piperidinyl) pyrimidine

A mixture containing 25 g (136.3 mmoles) of 2,4,6-trichloropyrimidine and 46.3 ml (272.6 mmoles) of 2,2,6,6,-tetramethylpiperidine is boiled under reflux for 50 hours, then the reaction mixture is cooled down and suspended in 250 ml of hexane. The insoluble part is filtered off, the filtrate (mother liquor) is evaporated and the residue is distributed between 300 ml of chloroform and 50 ml of 10% sodium hydroxide solution. After separation the organic phase is washed 4 times with 100 ml of water each, dried and evaporated. The residue is purified by chromatography on a silica gel column by using hexane as eluent. After recrystallization from hexane the title compound is obtained in a yield of 8.04 g (20.47%), m.p.:89°–900° C.

$^1$H-NMR (60 MHz, CDCl$_3$) δ ppm: 6.53 (s, 1H, 5-H).

EXAMPLE 33

Preparation of 4-chloro-2-(2,2,6,6-tetramethyl-1-piperidinyl)-6-pyrrolidinopyrimidine The reaction of 4,6-dichloro-2-(2,2,6,6-tetramethyl-1-piperidinyl) pyrimidine with pyrrolidine as described in Example 7 gives the title compound in a yield of 75.08%, m.p.:130°–135° C.

$^1$H-NMR (60 MHz, CDCl$_3$) δ ppm: 5.76 (s, 1H, 5-H).

Example 34

Preparation of 2-(2,2,6,6-tetramethyl-1-piperidinyl)-4-(1piperazinyl)-6-(1-pyrrolidinyl)pyrimidine 4-chloro-2-(2,2,6,6-tetramethyl-1-piperidinyl)-6-(1-pyrrolidinyl) pyrimidine is reacted with piperazine as described in Example 5 to obtain the title compound in a yield of 80.2%, m.p.:134°–137° C.

$^1$H-NMR (60 MHz, CDCl$_3$) δ ppm: 5.01 (s, 1H, 5-H).

Example 35

Preparation of 16α-methyl-21-{4-[2,(2,2,6,6-tetramethyl-1-piperidinyl)-6-pyrrolidino-4-pyrimidinyl]-1-piperazinyl}-pregna-1,4,9(11)-triene-3,20-dione The reaction of 16α-methyl-21-(4-bromobenzenesulfonyloxy)pregna-1,4,9(11)-triene-3,20-dione with 2-(2,2,6,6-tetramethyl 1-1-piperidinyl)-4-(piperazinyl)-6-pyrrolidinopyrimidine as described in Example 13 gives the title compound in a yield of 64.1%, m.p.:171°–181° C.

$^1$H-NMR (60 MHz, CDCl$_3$) δ ppm: 0.67 (s, 3H, 18-CH$_3$), 0.94 (s, 3H, 16α-CH$_3$), 1.40 (s, 3H, 19-CH$_3$), 1.48 (s, 12H, 4×tetramethylpiperidinyl-CH$_3$), 5.01 (s, 1H, pyrimidine C5-H), 5.51 (m, 1H, 11-H), 6.09 (br, 1H, 4-H), 6.27 (dd, 1H, 2-H), 7.20 (d, 1H, 1-H).

EXAMPLE 36

Preparation of 6-chloro-2-(1,1-dimethylethylamino)-4-(2,2-dimethylpropylamino)pyrimidine After dissolving 5.0 g of 4,6-dichloro-2-(1,1-dimethylethylamino)pyrimidine in 25 ml of isopropanol and adding 5 ml of 1-amino-2,2-dimethylpropane, the reaction mixture is boiled under reflux for 20 hours, then the reaction mixture is evaporated and the residue is distributed between 80 ml of chloroform and 15 ml of 10% sodium hydroxide solution. After separation the organic phase is washed 4 times with 20 ml of water each, then dried and evaporated. The residue is recrystallized from hexane to give the title compound in a yield of 4.49 g (73%), m.p.:109.5°–111° C.

$^1$H-NMR (60 MHz, CDCl$_3$) δ ppm: 5.71 (s, 1H, 5-H).

EXAMPLE 37

Preparation of 2-(1,1-dimethylethylamino)-4-(2,2-dimethylpropylamino)- 6-(1-piperazinyl)pyrimidine The reaction of 6-chloro-2-(1,1-dimethylethylamino)-4-(2,2-dimethylpropylamino)pyrimidine with piperazine as described in Example 5 gives the title compound in a yield of 86.0%, m.p.:120°–124° C.

$^1$H-NMR (60 MHz, CDCl$_3$) δ ppm: 4.96 (s, 1H, 5-H).

EXAMPLE 38

Preparation of
16α-methyl-21-{4-[2-(1,1-dimethylethylamino)-
4-(2,2-dimethylpropylamino)-6-pyrimidinyl]-
1-piperazinyl}-pregna- 1,4,9(11)-triene-3,20-dione 16α-Methyl-21-(4-nitrobenzenesulfonyloxy)pregna- 1,4,9(11)-triene-3,20-dione is reacted with 2,4-bis(4,4-ethylenedioxy- 1-piperidinyl)-6-(1-piperazinyl)pyrimidine as described in Example 6 to obtain the title compound in a yield of 85.7%, m.p.:155°–160° C.

$^1$H-NMR (60 MHz, CDCl$_3$) δ ppm: 0.68 (s, 3H, 18-CH$_3$), 0.96 and 0.98 (s, s, 12H, 16α-CH$_3$ és C(CH$_3$)$_3$), 1.39 (s, 9H, N(CH$_3$)$_3$), 1.40 (s, 3H, 19-CH$_3$), 4.97 (s, 1H, pyrimidine C5-H), 5.52 (m, 1H, 11-H), 6.10 (br, 1H, 4-H), 6.28 (dd, 1H, 2-H), 7.20 (d, 1H, 1-H).

EXAMPLE 39

Preparation of
21-{4-[2,4-bis(1-adamantylamino)-6-pyrimidinyl]
piperazinyl}-16α-methylpregna-1,4,9(11)-
triene-3,20-dione methanesulfonate After suspending 1.1 g (1.4 mmoles) of 21-{4-[2,4-bis(1-adamantylamino)-6-pyrimidinyl]-1-piperazinyl}-16α-methyl-pregna- 1,4,9(11)-triene-3,20-dione in 35 ml of anhydrous ethanol, 135 mg (1.4 moles) of methanesulfonic acid is added under stirring. After dissolution the solution is filtered and evaporated to dryness. The foam-like residue is suspended in ether and filtered off to obtain 1.18 g (95.5%) of the title compound.

EXAMPLE 40

Preparation of
2,4-bis(1-adamantylamino)-6-chloropyrimidine and
4,6-bis(1-adamantylamino)-2-chloropyrimidine 26.0 g (87.25 mmoles) of 4-(1-adamantylamino)-2,6-dichloropyrimidine and 39.5 g (261.6 mmoles) of 1-aminoadamantane are dissolved in 200 ml of n-butanol, the reaction mixture is boiled for 75 hours and evaporated. The residue is suspended in 400 ml of ether and filtered. The filtered substance is chromatographed after drying on a silica gel column by using chloroform as eluent. The substance obtained is a mixture of the title isomers. The isomers are separated on a silica gel column by using as eluent a 49:1 mixture of hexane and ethyl acetate. 2,4-Bis(1-adamantylamino)-6-chloropyrimidine is obtained which is recrystallized from hexane to obtain a yield of 21.67 g (60.14%). Its melting point and $^1$H-NMR are identical to those of the product according to Example 11.

By continuing the elution with a 6:1 mixture of the above solvents the more polar 4,6-bis(1-adamantylamino)-2-chloropyrimidine is obtained which is also recrystallized from hexane to result a yield of 1.88 g (5.22%), m.p.:260°–266° C.

$^1$H-NMR (60 MHz, CDCl$_3$) δ ppm: 5.49 (s, 1H, 5-H).

EXAMPLE 41

Preparation of
4,6-bis(1-adamantylamino)-2-(1-piperazinyl)pyrimidine 4,6-bis(1-adamantylamino)-2-chloropyrimidine is reacted with piperazine according to the method of Example 4 to obtain the title compound in a yield of 94.4%, m.p.:210°–220° C.

$^1$H-NMR (60 MHz, CDCl$_3$) δ ppm: 4.97 (s, 1H, 5-H).

EXAMPLE 42

Preparation of 21-{4-[4,6-bis(1-adamantylamino)-2-pyrimidi-yl]-1-piperazinyl}-16 α-methyl-pregna-1,4,9(11)-triene-3,20-dione 21-(4-Bromobenzenesulfonyloxy)-16α-methyl-pregna-1,4,9(11)-triene-3,20-dione is reacted with 4,6-bis(1-adamantylamino)- 2-(1-piperazinyl) pyrimidine according to the method of Example 6 to obtain the title compound in a yield of 52.9%, m.p.:190°–200° C.

$^1$H-NMR (300 MHz, CDCl$_3$) δ ppm: 0.68 (s, 3H, 18-CH$_3$), 0.96 (d, 3H, 16α-CH$_3$), 1.40 (s, 3H, 19-CH$_3$), 1.67, 2.02 and 2.09 (br, br, br, 30H, adamantyl-CH and-CH$_2$), 3.07 and 3.19 (d, d, 1H, 1H, 21-CH$_2$), 4.23 (vbr, 2H, 2xNH), 4.96 (s, 1H, pyrimidine C5-H), 5.51 (m, 1H, 11-H), 6.07 (m, 1H, 4-H), 6.29 (dd, 1H, 2-H), 7.17 (d, 1H, 1-H).

EXAMPLE 43

Preparation of
2-(cyclopentylamino)-4,6-dichloropyrimidine and
4-(cyclopentylamino)-2,6-dichloropyrimidine 2,4,6-Trichloropyrimidine is reacted with cyclopentylamine according to the method of Example 3. The less polar 2-(cyclopentylamino)-4,6-dichloropyrimidine is obtained in a yield of 35.2%, m.p.:48°–52° C.

$^1$H-NMR (60 MHz, CDCl$_3$) δ ppm: 6.52 (s, 1H, 5-H).

The more polar 4-(cyclopentylamino)-2,6-dichloropyrimidine is obtained as an oil in a yield of 57.2%

$^1$H-NMR (60 MHz, CDCl$_3$) δ ppm: 6.30 (s, 1H, 5-H).

EXAMPLE 44

Preparation of
2,4-bis(cyclopentylamino)-6-chloropyrimidine 5.0 g of 2-(cyclopentylamino)-4,6-dichloropyrimidine are dissolved in 25 ml of isopropanol, 7.5 ml of cyclopentylamine are added thereto and the reaction mixture is boiled for 6 hours. Then the reaction mixture is evaporated, the residue is separated between 80 ml of chloroform and 15 ml of 10% sodium hydroxide solution. After separation the organic phase is washed 4 times with 20 ml of water each, then dried and evaporated. The title compound is obtained after recrystallization from hexane in a yield of 5.24 g (86.7%), m.p.:94°–98° C.

$^1$H-NMR (60 MHz, CDCl$_3$) δ ppm: 5.67 (s, 1H, 5-H).

Example 45

Preparation of
2,4-bis(cyclopentylamino)-6-(1-piperazinyl)-pyrimidine 2,4-Bis(cyclopentylamino)-6-chloropyrimidine is reacted with piperazine according to the method of Example 4. The title compound is obtained in a yield of 81.9%, m.p.:142°–148° C.

$^1$H-NMR (60 MHz, CDCl$_3$) δ ppm: 4.94 (s, 1H, 5-H).

EXAMPLE 46

Preparation of 21-{4-[2,4-bis(cyclopentylamino)-6-pyrimidinyl]-1-piperazinyl}-16α-methyl-pregna-1,4,9(11)-triene-3,20-dione 21-(4-Bromobenzenesulfonyloxy)-16α-methyl-pregna-1,4,9(11)-triene-3,20-dione is reacted with 2,4-bis(cyclopentylamino)- 6-(1-piperazinyl)pyrimidine according to the method of Example 6 to obtain the title compound in a yield of 73.1%, m.p.:180°–185° C.

$^1$H-NMR (300 MHz, CDCl$_3$) δ ppm: 0.69 (s, 3H, 18-CH$_3$), 0.96 (d, 3H, 16α-CH$_3$), 1.40 (s, 3H, 19-CH$_3$), 3.12 and 3.21 (d, d, 1H, 1H, 21-CH$_2$), 3.88 and 4.19 (m, m, 1H, 2xN-CH<), 4.58 and 4.62 (vbr, vbr, 1H, 1H, 2xNH), 4.93 (s, 1H, pyrimidine C5-H), 5.51 (m, 1H, 11-H), 6.07 (m, 1H, 4-H), 6.28 (dd, 1H, 2-H), 7.16 (d, 1H, ! -H).

EXAMPLE 47

Preparation of an injectable solution

After dissolving 0.05% by weight of sodium pyrosulfite in deoxygenated water for injection use, the active agent is dissolved in the above solution. Simultaneously, 0.1% by weight of potassium sorbate is dissolved in deoxygenated water for injection use and an amount of sodium chloride required for isotonization is dissolved therein. The two above solutions are mixed, filled up to the desired final volume with deoxygenated water for injection use and finally, the solution is filtered through a membrane filter with a 0.2 μm mean pore size until free of bacteria and foreign materials. The solution is filtered and filled into ampoules under nitrogen.

A preferable composition of an injection of 1 ml volume is e.g. as follows:

| | |
|---|---|
| active ingredient | 10 mg |
| sodium pyrosulfite | 5 mg |
| sodium chloride | 7 mg |
| water for injection use, up to | 1 ml |

We claim:

1. 21-{4-[2,4-bis(1-adamantylamino)-6-pyrimidinyl]-1piperazinyl}- 16α-methylpregna-1,4,9(11)-triene-3,20-dione, or a pharmaceutically acceptable acid addition salt thereof.

2. The pharmaceutically acceptable acid addition salt of the compound of the Formula (I) defined in claim 1 which is 21-{4-[2,4-bis(1-adamantylamino)-6-pyrimidinyl]-1-piperazinyl}-16α-methylpregna-1,4,9(11)-triene-3,20-dione methanesulfonate.

3. A pharmaceutical composition, which comprises as active ingredient a therapeutically effective amount of a compound of formula (I), as defined in claim 1 or a pharmaceutically acceptable acid addition salt thereof, in combination with a pharmaceutically acceptable inert carrier.

4. A method for inhibiting the peroxidation of lipids, which comprises the step of administering to a mammalian subject in need of said treatment a therapeutically effective amount of a compound of the formula (I) as defined in claim 1, or a pharmaceutically acceptable acid addition salt thereof alone or in the form of a pharmaceutical composition.

* * * * *